(12) United States Patent
Giesing (10) Patent No.: US 9,636,488 B2
(45) Date of Patent: May 2, 2017

(54) DRUG DELIVERY SYSTEMS AND METHODS FOR TREATMENT OF PROSTATE

(71) Applicant: TARIS Biomedical LLC, Lexington, MA (US)

(72) Inventor: Dennis Giesing, Lee's Summit, MO (US)

(73) Assignee: TARIS Biomedical LLC, Lexington, MA (US)

( * ) Notice: Subject to any disclaimer, the term of this patent is extended or adjusted under 35 U.S.C. 154(b) by 0 days.

(21) Appl. No.: 14/628,874

(22) Filed: Feb. 23, 2015

(65) Prior Publication Data

US 2015/0165177 A1 Jun. 18, 2015

Related U.S. Application Data

(63) Continuation of application No. PCT/US2013/057841, filed on Sep. 3, 2013.

(60) Provisional application No. 61/696,029, filed on Aug. 31, 2012.

(51) Int. Cl.
| | |
|---|---|
| *A61K 31/7068* | (2006.01) |
| *A61M 31/00* | (2006.01) |
| *A61K 9/00* | (2006.01) |
| *A61K 45/06* | (2006.01) |

(52) U.S. Cl.
CPC ......... *A61M 31/002* (2013.01); *A61K 9/0034* (2013.01); *A61K 31/7068* (2013.01); *A61K 45/06* (2013.01); *A61M 2205/04* (2013.01); *A61M 2210/1085* (2013.01); *A61M 2210/166* (2013.01)

(58) Field of Classification Search
CPC A61K 31/7068; A61K 9/0034; A61M 31/002
See application file for complete search history.

(56) References Cited

U.S. PATENT DOCUMENTS

| | | |
|---|---|---|
| 6,171,298 B1 | 1/2001 | Matsuura et al. |
| 8,343,516 B2 | 1/2013 | Daniel et al. |
| 8,679,094 B2 | 3/2014 | Cima et al. |
| 8,690,840 B2 | 4/2014 | Lee et al. |
| 8,801,694 B2 | 8/2014 | Lee et al. |
| 9,017,312 B2 | 4/2015 | Lee et al. |
| 9,107,816 B2 | 8/2015 | Lee et al. |
| 2004/0260272 A1 | 12/2004 | Friedman et al. |
| 2009/0149833 A1 | 6/2009 | Cima et al. |
| 2010/0015200 A1 | 1/2010 | McClain et al. |
| 2010/0331770 A1 | 12/2010 | Lee et al. |
| 2011/0152839 A1 | 6/2011 | Cima et al. |
| 2012/0157917 A1 | 6/2012 | Schroeder |
| 2012/0203203 A1 | 8/2012 | Lee et al. |
| 2013/0324946 A1 | 12/2013 | Tobias et al. |
| 2014/0276636 A1 | 9/2014 | Lee et al. |
| 2015/0182516 A1 | 7/2015 | Giesing |

FOREIGN PATENT DOCUMENTS

| | | |
|---|---|---|
| EP | 1 913 962 A1 | 4/2008 |
| WO | 2006/030431 A2 | 3/2006 |
| WO | 2009/139984 A2 | 11/2009 |
| WO | 2010/151893 A1 | 12/2010 |
| WO | 2011/031855 A2 | 3/2011 |
| WO | 2011/089604 A2 | 7/2011 |
| WO | 2012/048114 A1 | 4/2012 |
| WO | 2012/096985 A1 | 7/2012 |
| WO | 2014/036556 A2 | 3/2014 |
| WO | 2014/145638 A1 | 9/2014 |
| WO | 2015/026813 A1 | 2/2015 |

OTHER PUBLICATIONS

Morant et al., Ann. Oncol., 2000, 11, p. 183-188.*
Jantscheff et al., Prostate, 2009, 69, p. 1151-1163.*
Campodonico et al., "Intravesical Gemcitabine in Recurrent Superficial Bladder Carcinoma: Preliminary Results on Ablative Efficacy and Tolerability," Anticancer Research, 2005, 25:2381-2384.
Laufer et al., "Intravesical Gemcitabine Therapy for Superficial Transitional Cell Carcinoma of the Bladder: A Phase I and Pharmacokinetic Study," Journal of Clinical Oncology, 2003, 21(4):697-703.
Singapore Search Report and Written Opinion for SG Application No. 11201501483X mailed Jan. 5, 2016 (11 pages).
PCT International Search Report and Written Opinion for PCT Application No. PCT/US2013/057841 mailed Feb. 14, 2014 (18 pages).
PCT International Search Report and Written Opinion for PCT Application No. PCT/US2015/019262 mailed May 22, 2015 (15 pages).
Horinaga et al., "Enhanced Antitumor Effect of Coincident Intravesical Gemcitabine Plus BCG Therapy in an Orthotopic Bladder Cancer Model," Urology, 2010, 76(5):1267.e1-1267.e6.
Nativ et al., "Antineoplastic Effect of Gemcitabine in an Animal Model of Superficial Bladder Cancer," Urology, 2004, 54(4):845-848.
Shelley et al., "Intravesical Gemcitabine Therapy for Non-Muscle Invasive Bladder Cancer (NMIBC):A Systematic Review," BJU International, 2012, 496-505.
Xinwu et al., "Effect of Intravesical Instillation Capecitabine Combined with Oxaliplatin on the Recurrence of Bladder cancer," Anti-Tumor Pharmacy, 2011, 1(3)203-205.
Hendricksen et al., "Intravesical gemcitabine: an update of clinical results," Urology, 2006, 16:361-366.

\* cited by examiner

*Primary Examiner* — Jonathan S Lau
(74) *Attorney, Agent, or Firm* — Eversheds Sutherland (US) LLP (57) ABSTRACT

Methods, devices, and medicaments that include a drug are provided for use in the treatment of the prostate by locally administering the drug into the bladder of a patient to achieve a sustained concentration of the drug in urine in the bladder sufficient to produce a therapeutic concentration of the drug in the prostate. The drug may be delivered into the bladder from an intravesical drug delivery device inserted into the bladder, wherein the device continuously releases the drug into the urine in the bladder over an extended period of hours or days.

21 Claims, 11 Drawing Sheets

DRUG DELIVERY SYSTEMS AND METHODS FOR TREATMENT OF PROSTATE

CROSS-REFERENCE TO RELATED APPLICATIONS

This application is a continuation of PCT/US2013/057841, filed 3 Sep. 2013, which claims the benefit of U.S. Provisional Patent Application No. 61/696,029, filed Aug. 31, 2012, which are incorporated herein by reference.

BACKGROUND

Delivery of diagnostic or therapeutic agents to the prostate is difficult. Current practice requires systemic administration, such as by intravenous, intramuscular, oral, transdermal, or intranasal routes, using doses which result in significant exposure to healthy tissues and relatively low exposure within the prostate gland. Frequently the systemic exposure leads to unwanted or harmful side effects which limit the usefulness of the therapeutic agent in treating prostate disease.

Targeted and local delivery strategies have been explored to minimize peripheral exposure with limited success. Some targeting strategies rely on prostate cells to express specific receptors to which a drug-targeting ligand complex binds. These receptors may not always be present, limiting the utility of the approach. The receptor density on prostate cells also can vary widely and restrict the actual amount of drug delivered to the prostate. In addition, other cells in the body may also express the same receptor leading to unwanted drug exposure. Lastly, the drug targeting ligand complex can be degraded prior to reaching the prostate, defeating the targeting mechanism.

Direct injection into or near the prostate also has been tried. Patient acceptance is low due to the pain and risk of infection. In addition, the mean residence time of the drug often is relatively short, which necessitates the use of multiple injections for treatment. Furthermore, the disruption of prostate tumors during injection can lead to metastasis. Depot formulations extend the drug presence in the prostate but reduce the amount of drug that can be injected into the prostate and may enhance local tissue toxicity.

Radionucleotide-containing pellets placed near the prostate are used to treat prostate cancer but provide only one treatment modality. Radiation therapy is also non-selective, leading to significant damage to surrounding healthy tissue structures including nerves.

The use of a suppository or drug eluting stent placed in the prostatic urethra is known, but these are difficult to place and poorly tolerated in men. Furthermore, these delivery means have a limited payload capacity.

Accordingly, there remains a need for improved drug delivery methods and systems for treating the prostate, such as in the treatment of prostate cancer or prostatitis.

SUMMARY

In one aspect, a medicament is provided that includes gemcitabine for use in the treatment of the prostate by locally administering the gemcitabine into the bladder of a patient to achieve a sustained concentration of the drug in the urine in the bladder sufficient to produce a therapeutic concentration of the drug in the prostate, wherein the locally administering into the patient's bladder is at a mean average amount of from 1 mg to about 300 mg per day. The locally administering of gemcitabine may be continuous or intermittent. In one embodiment, the patient is in need of treatment for prostate cancer. In an embodiment, the gemcitabine is delivered into the bladder from an intravesical drug delivery device which continuously releases the gemcitabine into the urine in the bladder over a sustained period. In an alternative embodiment, the gemcitabine is delivered into the bladder from a coating substance applied to the bladder, which coating substance continuously releases the gemcitabine into the urine in the bladder over a sustained period. The coating substance may include a mucoadhesive formulation. In a further alternative embodiment, a liquid form of the gemcitabine is pumped into the bladder through a urethral catheter inserted into the bladder. In various embodiments, the gemcitabine is released into the patient's bladder continuously over a period of at least 2 hours, such as from 1 day to 14 days. In an embodiment, the gemcitabine is released into the patient's bladder at a mean average amount of from 1 mg to about 100 mg gemcitabine per day for up to 7 days. In another embodiment, the gemcitabine is released into the patient's bladder at a mean average amount of from 20 mg to 300 mg per day for up to 7 days.

In another aspect, a medical device is provided for intravesical administration of gemcitabine. In an embodiment, the medical device includes a housing configured for intravesical insertion and a dosage form including gemcitabine, wherein the housing holds the dosage form and is configured to release the gemcitabine into the bladder in an amount therapeutically effective for the treatment of the prostate, and wherein the device is configured to release gemcitabine into the bladder at a mean average amount of from 1 mg to about 300 mg per day of the gemcitabine. The gemcitabine contained in the housing may be in a non-liquid form. The housing may be elastically deformable between a retention shape configured to retain the device in a patient's bladder and a deployment shape for passage of the device through the patient's urethra. In an embodiment, the device is configured to release from 1 mg to 100 mg of gemcitabine per day for up to 7 days. In another embodiment, the device is configured to release from 20 mg to 300 mg of gemcitabine per day for up to 7 days.

In still another aspect, a method is provided of administering a drug to a patient in need of treatment of the prostate. The method includes locally administering gemcitabine into the bladder of a patient to achieve a sustained concentration of the gemcitabine in urine in the bladder sufficient to produce a therapeutic concentration of the gemcitabine in the prostate. In one embodiment, the method includes administering at least a second therapeutic agent to the patient. The second therapeutic agent may be administered intravesically. The second therapeutic agent may include a cytotoxic agent, an analgesic agent, an anti-inflammatory agent, or a combination thereof. The second therapeutic agent may prevent, treat, or ameliorate cystitis of the bladder.

DETAILED DESCRIPTION

It has been discovered that intravesical administration can be used to deliver a therapeutically effective amount of gemcitabine to a patient's prostate over a short or extended period while minimizing systemic exposure of the drug. For example, a controlled amount of drug may be dissolved in urine in the patient's bladder in a concentration and over a time sufficient to produce therapeutic concentrations of the drug in the prostate. Because the bladder limits the absorption of urine components into the general circulation, systemic exposure to the drug is advantageously minimized.

A variety of methods can be used to achieve the required urine concentrations of the gemcitabine. In one embodiment, the drug can be provided by direct instillation of a simple solution into the bladder. For example, a solution of the drug may be pumped into the bladder through a urethral or suprapubic catheter in a continuous or pulsatile manner over the treatment period. In another embodiment, the drug is released from a device or composition deployed in the bladder, wherein the device or composition releases the drug (continuously or intermittently) at a rate effective to produce the desired concentration of drug in the urine over a specified treatment period. For example, the drug may be released from an intravesically-inserted device into the bladder and then the drug diffuses from the bladder to the prostate. At the end of the treatment period, the device may be retrieved from the bladder, or it may be eliminated by being resorbed, dissolved, excreted, or a combination thereof.

In a preferred embodiment, the drug is gemcitabine, which is effective in treating prostate cancer. The therapeutic utility of gemcitabine to treat prostate diseases is thought to be the result of the unique combination of the compound's physical and chemical properties which facilitate prostate uptake following intravesical administration and high intrinsic drug potency toward prostate tumor cells. See Examples below.

In other embodiments, the drug may be essentially any suitable drug, including but not limited to ones useful in the treatment of prostate cancer, benign prostatic hyperplasia, or prostatitis. For example, the drug may be an antibiotic, an alpha blocker, an anti-inflammatory, an alpha 1A antiadrenergic, an antiandrogen, a microtubule inhibitor, or a 5 alpha reductase inhibitor. Examples of other drugs include but are not limited to ciproflaxin, trimethoprim, docetaxel, and finasteride.

In a preferred embodiment, the drug is administered to the prostate from an intravesical device. Preferred examples of intravesical drug delivery devices and methods of deploying those devices into the bladder are described in the following U.S. Patent Application Publications: US 2012/0203203 (Lee et al.); US 2012/0089122 (Lee et al.); US 2012/0089121 (Lee et al.); US 2011/0218488 (Boyko et al.); US 2011/0202036 (Boyko et al.); US 2011/0152839 (Cima et al.); US 2011/0060309 (Lee et al.); US 2010/0331770 (Lee et al.); US 2010/0330149 (Daniel et al.); US 2010/0003297 (Tobias et al.); US 2009/0149833 (Cima et al.); and US 2007/0202151 (Lee et al.).

In embodiments in which the drug is delivered from an intravesical drug delivery device, the drug may be housed in the device in various forms, which may depend on the particular mechanism by which the device controllably releases the drug into fluid (e.g., urine) in the bladder. In some embodiments, the drug is provided in a solid, semi-solid, or other non-liquid form, which advantageously may facilitate stable storage of the drug before the device is used and advantageously may enable the drug payload of the device to be stored in smaller volume than would be possible if the drug were housed in the form of a liquid solution. In an embodiment the non-liquid form is selected from tablets, granules, semisolids, capsules, and combinations thereof. In one embodiment, the drug is in the form of a plurality of tablets, such as mini-tablets described in U.S. Pat. No. 8,343,516. In other embodiments, the drug may be housed in a liquid form, such as in a solution with a pharmaceutically acceptable excipient.

Figure 1A:
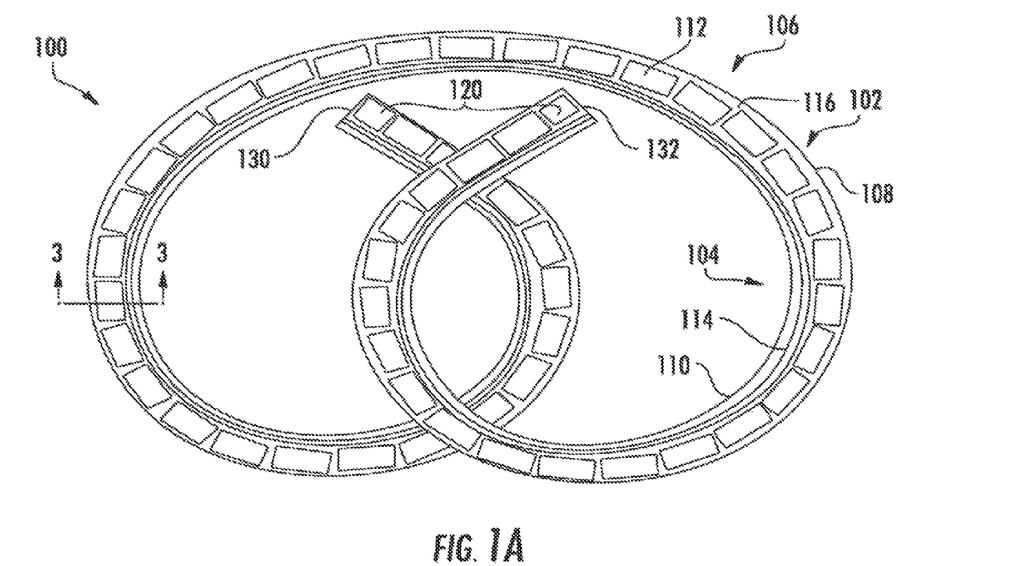
FIGS. 1A-1B illustrate one embodiment of an intravesical drug delivery device that may be used for administering gemcitabine as described herein.

An embodiment of a drug delivery device 100 is illustrated in FIG. 1A. The device 100 includes a device body having a drug reservoir portion 102 and a retention frame portion 104. In FIG. 1, the device 100 is shown in a relatively expanded shape suited for retention in the body. Following deployment into the body, the device 100 may assume the relatively expanded shape to retain the drug delivery device in the body cavity or lumen.

For the purposes of this disclosure, terms such as "relatively expanded shape", "relatively higher-profile shape", or "retention shape" generally denote any shape suited for retaining the device in the intended implantation location, including but not limited to the pretzel shape shown in FIG. 1 that is suited for retaining the device in the bladder. Similarly, terms such as "relatively lower-profile shape" or "deployment shape" generally denote any shape suited for deploying the drug delivery device into the body, including a linear or elongated shape that is suited for deploying the device through the working channel of catheter, cystoscope, or other deployment instrument positioned in the urethra. In embodiments, the drug delivery device may naturally assume the relatively expanded shape and may be deformed, either manually or with the aid of an external apparatus, into the relatively lower-profile shape for insertion into the body. Once deployed the device may spontaneously or naturally return to the initial, relatively expanded shape for retention in the body.

In the illustrated embodiment, the drug reservoir and retention frame portions 102, 104 of the drug delivery device 100 are longitudinally aligned and are coupled to each other along their length, although other configurations are possible. The drug delivery device 100 includes an elastic or flexible device body 106 that defines a drug reservoir lumen 108 (i.e., the drug housing) and a retention frame lumen 110.

The drug reservoir lumen 108 is designed to house a drug formulation that comprises the drug. In the illustrated embodiment, the drug formulation is in the form of a number of solid drug tablets 112. The retention frame lumen 110 is designed to house a retention frame 114 to form the retention frame portion 104. The illustrated lumens 108, 110 are discrete from each other, although other configurations are possible.

Figure 1B:
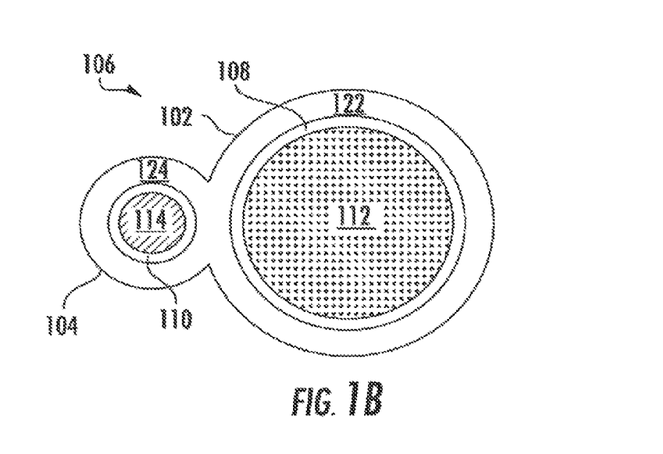

As shown in the cross-sectional view of FIG. 1B, the device body 106 includes a tube or wall 122 that defines the drug reservoir lumen 108 and a tube or wall 124 that defines the retention frame lumen 110. The tubes 122, 124 and lumens 108, 110 can be substantially cylindrical, with the drug reservoir lumen 108 having a relatively larger diameter than the retention frame lumen 110, although other configurations can be selected based on, for example, the amount of drug to be delivered, the diameter of the retention frame, and deployment considerations such as the inner diameter of the deployment instrument. The wall 124 that defines the retention frame lumen 110 may extend along the entire length of the wall 122 that defines the drug reservoir lumen 108, so that the retention frame lumen 110 has the same length as the drug reservoir lumen 108 as shown, although one wall may be shorter than the other wall in other embodiments. The two walls 122, 124 are attached along the entire length of the device in the illustrated embodiment, although intermittent attachment can be employed.

As shown in FIG. 1A, the drug reservoir lumen 108 is loaded with a number of drug units 112 in a serial arrangement. Essentially any number of drug units may be used, for example, depending upon the sizes of the reservoir and the drug units. The drug reservoir lumen 108 includes a first end opening 130 and an opposed second end opening 132. Once the drug units 112 are loaded, restraining plugs 120 are disposed in the openings 130 and 132. The restraining plugs 120, in this embodiment, are cylindrical plugs secured into the entry 130 and the exit 132. In other embodiments, the openings 130 and 132 are closed off with other structures or materials, which may, depending on the particular embodiments, include an aperture or a water- or drug-permeable wall to facilitate ingress or egress of water or drug during use.

The retention frame lumen 110 is loaded with the retention frame 114, which may be an elastic wire. The retention frame 110 may be configured to return spontaneously to a retention shape, such as the illustrated example "pretzel" shape or another coiled shape, such as those disclosed in the applications previously incorporated. In particular, the retention frame 114 may retain the device 100 in the body, such as in the bladder. For example, the retention frame 114 may have an elastic limit and modulus that allows the device 100 to be introduced into the body in a relatively lower-profile shape, permits the device 100 to return to the relatively expanded shape once inside the body, and impedes the device from assuming the relatively lower-profile shape within the body in response to expected forces, such as the hydrodynamic forces associated with contraction of the detrusor muscle and urination. Thus, the device 100 may be retained in the body once implanted, limiting or prevent accidental expulsion.

The material used to form the device body 106, at least in part, may be elastic or flexible to permit moving the device 100 between deployment and retention shapes. When the device is in the retention shape, the retention frame portion 104 may tend to lie inside the drug reservoir portion 102 as shown, although the retention frame portion 104 can be positioned inside, outside, above, or below the drug reservoir portion 102 in other cases.

The material used to form the device body 106 may be water permeable so that solubilizing fluid (e.g., urine or other bodily fluid) can enter the drug reservoir portion 102 to solubilize the drug units 112 once the device is implanted. For example, silicone or another biocompatible elastomeric material may be used. In other embodiments, the device body may be formed, at least in part, of a water-impermeable material.

Figure 2A:
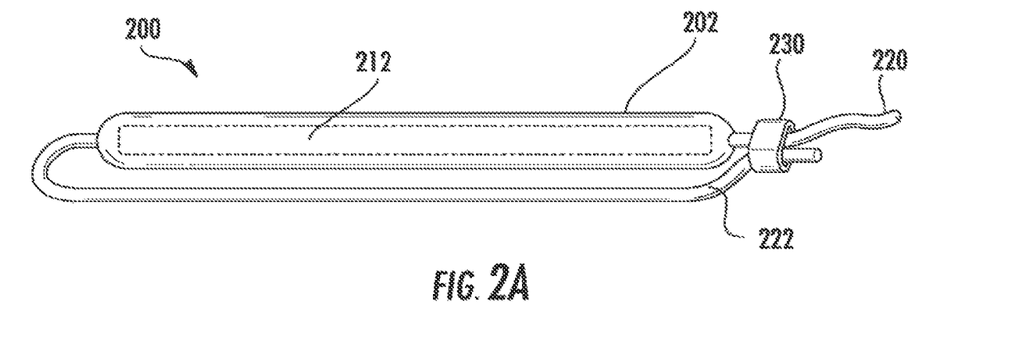
FIGS. 2A-2B illustrate another embodiment of an intravesical drug delivery device that may be used for administering gemcitabine as described herein.

FIG. 2A illustrates an implantable drug delivery device 200, which includes a drug reservoir 202 loaded with drug 212 and a retention structure that includes two filaments 220, 222 associated with a fastener 230. As shown, the drug reservoir 202 is an elongated tube that can be deformed between a relatively linear deployment shape, such as the shape shown in FIG. 2A, and a relatively circular retention shape, such as the shape shown in FIG. 2B. The drug 212 may be loaded in the tube in a flexible form, so that the drug reservoir 102 can be moved between the two shapes. For example, the drug 212 may be a number of solid drug tablets, a liquid, or a gel. The filaments 220, 222 may be attached to opposite ends of the drug reservoir 202 and joined by the fastener 230. The fastener 230 can be adjusted to adjust the position of one filament 220 with reference to the other 222, thereby adjusting the position of one end of the drug reservoir 202 with reference to the other end. The device 200 can assume the retention shape by adjusting the filaments 220, 222 to draw the ends of the drug reservoir 202 closer together, and thereafter the device 200 can be retained in the retention shape by preventing adjustment of the filaments 220, 222 with the fastener 230. In such an embodiment, the device 200 is manually adjusted into the retention shape by manually adjusting the filaments 220, 222 after the device 200 is inserted into the bladder.

Figure 2B:
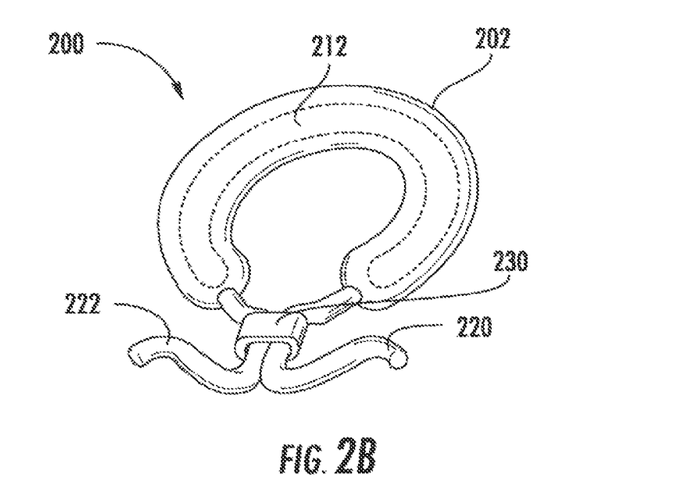

In the illustrated embodiment, the fastener 230 is a cinch nut that permits shortening the portion of the filaments 220, 222 between the drug reservoir ends and the cinch nut, but prevents lengthening of these portions of the filaments 220, 222. Thus, the ends of the drug reservoir 202 can be drawn closer together by pulling one or both of the filaments 220, 222 through the cinch nut, causing the device 200 to assume the retention shape. Once the filaments 220, 222 have been so adjusted, the cinch nut prevents lengthening of the filaments 220, 222, retaining the device in the retention shape. Thus, manually adjusting the device 200 into the retention shape once implanted merely requires pulling one or both of the filaments 220, 222, although other fasteners 230 that require separate manipulation can be employed. Other fasteners may also be used.

Figure 3A:
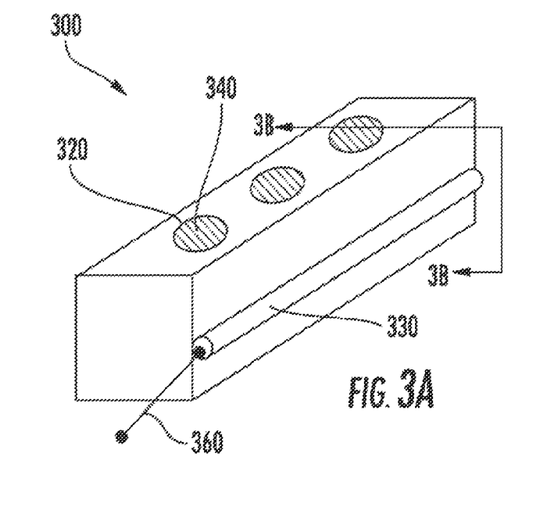
FIGS. 3A-3C illustrate still another embodiment of an intravesical drug delivery device that may be used for administering gemcitabine as described herein.
Figure 3B:
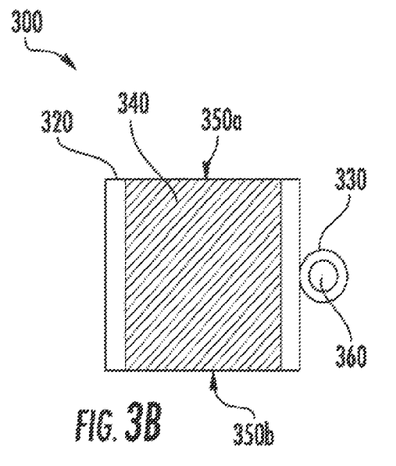
Figure 3C:
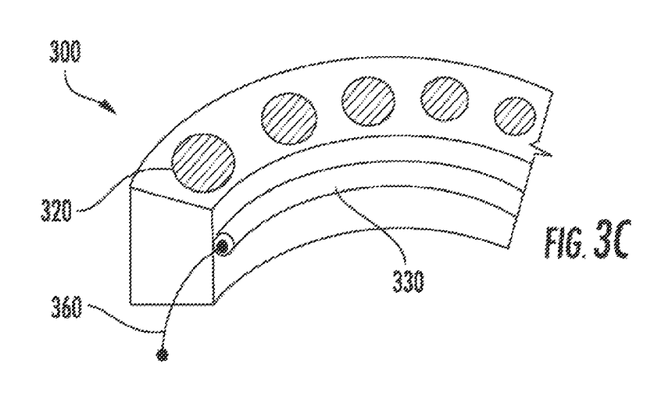

Another embodiment of an intravesical drug delivery device is illustrated in FIGS. 3A-3C. In this embodiment, the device includes a housing 300 having a single, continuous structure with multiple, discrete drug reservoir lumens 320 and optionally having at least one retention frame lumen 330 in which a retention frame 360 is disposed. Each drug reservoir lumen 320 has two defined openings, as shown in FIG. 3B, and is dimensioned to hold at least one solid drug unit 340. Solid drug unit 340 may be a drug tablet or capsule. In other embodiments not shown, each drug reservoir lumen has one defined opening. The housing may be formed of a flexible polymer, such as silicone. FIG. 3B is a cross-sectional view of the plane that bisects one of the drug reservoir lumens 320 of the housing shown in FIG. 3A along line 3B-3B. As shown in FIG. 3B, the monolithic housing 300 has two defined openings (350a, 350b) in its drug reservoir lumen 320 that expose both ends of the solid drug unit 340. The retention frame lumen 330, in this embodiment, is aligned parallel to the longitudinal axis of the housing and perpendicular to the drug reservoir lumen 320. FIG. 3C is a perspective view of a portion of the embodiment of the device 300 shown in FIG. 3A when the device is in its retention shape, which is taken when the retention frame 360 is disposed in the retention frame lumen 330. The drug reservoir lumens 320 and the retention frame 360 in the housing of this embodiment are oriented so that the drug reservoir lumens 320 are outside the retention frame's 360 arc. Alternatively, the housing in FIG. 3C can be rotated 180 degrees about the retention frame 360 to yield a configuration in which the drug reservoir lumens 320 are arranged within the retention frame's 360 arc. With this embodiment, the devices provide sufficient direct contact between solid drug units and with urine surrounding the device when deployed and retained in the bladder. In embodiments, release of the drug from the device is controlled by erosion of an exposed portion of the surface of a solid drug unit, such that the rate of drug release from the drug delivery device may be directly proportional to and limited by the total exposed surface area of the solid drug units.

Figure 4A:
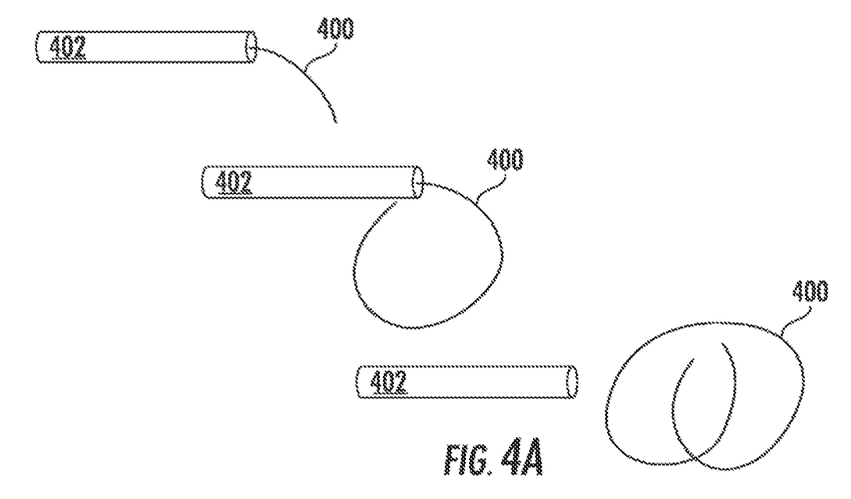
FIGS. 4A-4B illustrate a method of inserting an intravesical drug delivery device into the bladder of a patient for local administration of gemcitabine as described herein.
Figure 4B:
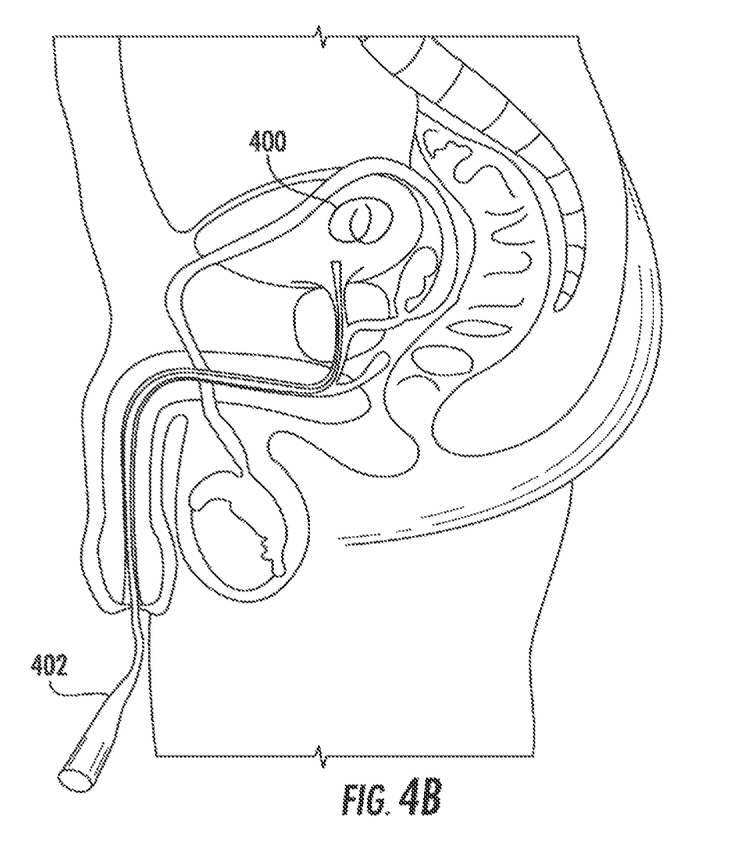

One embodiment of inserting an intravesical device 400 for subsequent controlled release of the drug into the bladder is shown in FIGS. 4A and 4B. Here, the device 400 is shown assuming a retention shape as the device exits a deployment instrument 402. The deployment instrument 402 may be any suitable device. It may be a lumenal device, such as a catheter, urethral catheter, or cystoscope. The deployment instrument 402 may be a commercially available device or a device specially adapted for the present drug delivery devices. FIG. 4B illustrates the insertion of the device 400 into the bladder, wherein the adult male anatomy is shown by way of example. The deployment instrument 402 is inserted through the urethra to the bladder, and the device 400 may be passed from/through the deployment instrument 402, driven by a stylet or flow of lubricant or combination thereof until the device 400 exits into the bladder, and as shown is in a retention shape.

In various embodiments, the drug may be released from the intravesical drug delivery device by diffusion to through a wall of the drug housing, by diffusion to through one or more defined apertures in a wall of the drug housing, by osmotic pressure through an aperture in the drug housing, by erosion of a drug formulation in contact with urine in the bladder, or by a combination thereof.

In some embodiments in which the device comprises a drug in a solid form, elution of drug from the device occurs following dissolution of the drug within the device. Bodily fluid enters the device, contacts the drug and solubilizes the drug, and thereafter the dissolved drug diffuses from the device or flows from the device under osmotic pressure or via diffusion. For example, the drug may be solubilized upon contact with urine in cases in which the device is implanted in the bladder.

In various embodiments, the intravesical device may release the drug continuously or intermittent to achieve a concentration of the drug in the bladder that produces a sustained, therapeutically effective concentration of the drug in the prostate over a period from 1 hour to 1 month, for example from 2 hours to 2 weeks, from 6 hours to 1 week, from 24 hours to 72 hours, etc.

In various embodiments, the intravesical device may release the gemcitabine or other drug in an amount of from 1 mg/day to 100 mg/day, for example from 20 mg/day to 300 mg/day or from 25 mg/day to 300 mg/day.

Figure 5A:
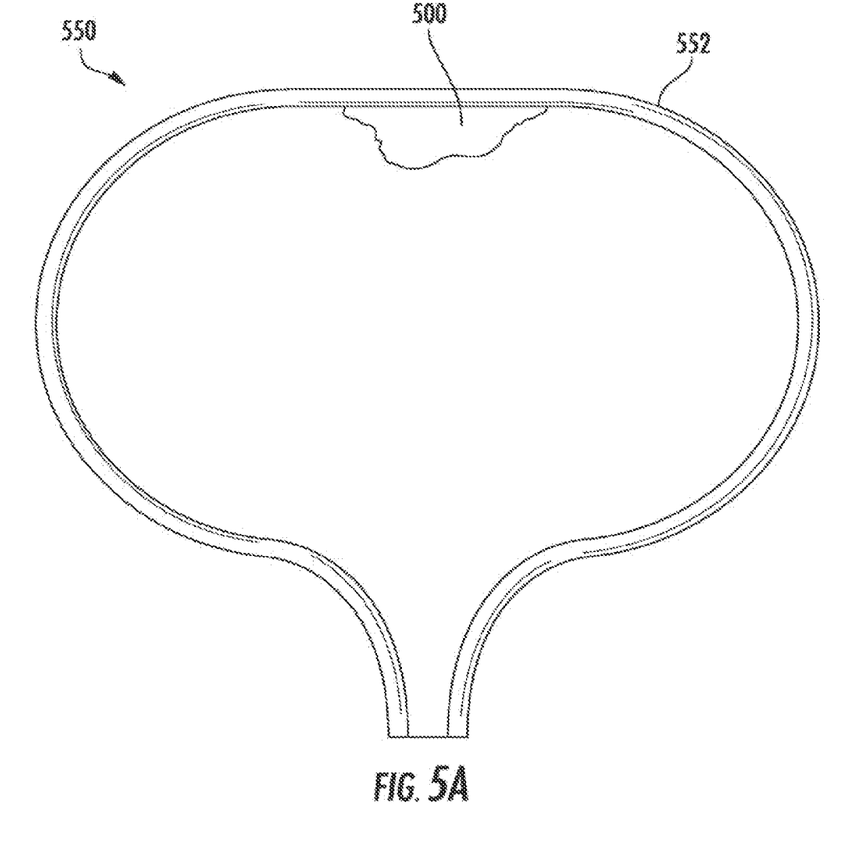
FIG. 5A illustrates a material applied to the inner surface of the bladder wall for local administration of gemcitabine as described herein.

In another embodiment, a coating substance may be intravesically applied to the bladder wall, wherein the coating substance includes the gemcitabine or other drug and one or more excipient materials that promote adherance of the coating substance to the bladder wall and provides continuous controlled release of the drug over the treatment period. The coating substance may be a mucoadhesive formulation, such as gels, ointments, creams, films, emulsion gels, tablets, polymers, or a combination thereof. Mucoadhesive formulation polymers may include hydrogels or hydrophilic polymers, polycarbophil (i.e. Carbopols, etc.), chitosan, polyvinylpyrrolidone (PVP), lectin, polyethyleneglycolated polymers, celluloses, or a combination thereof. Suitable celluloses include methyl cellulose (MC), carboxymethyl cellulose (CMC), hydroxypropyl cellulose (HPC), or combinations thereof. The coating substance may include a permeation enhancer. Non-limiting examples of permeation enhancers include dimethyl sulfoxide (DMSO), sodium carboxymethyl cellulose (NaCMC), lipids, surfactants, or combinations thereof. As shown in FIG. 5A, a coating substance 500 may be deployed in the bladder 550 so that the coating substance 500 engages the bladder wall 552.

Figure 5B:
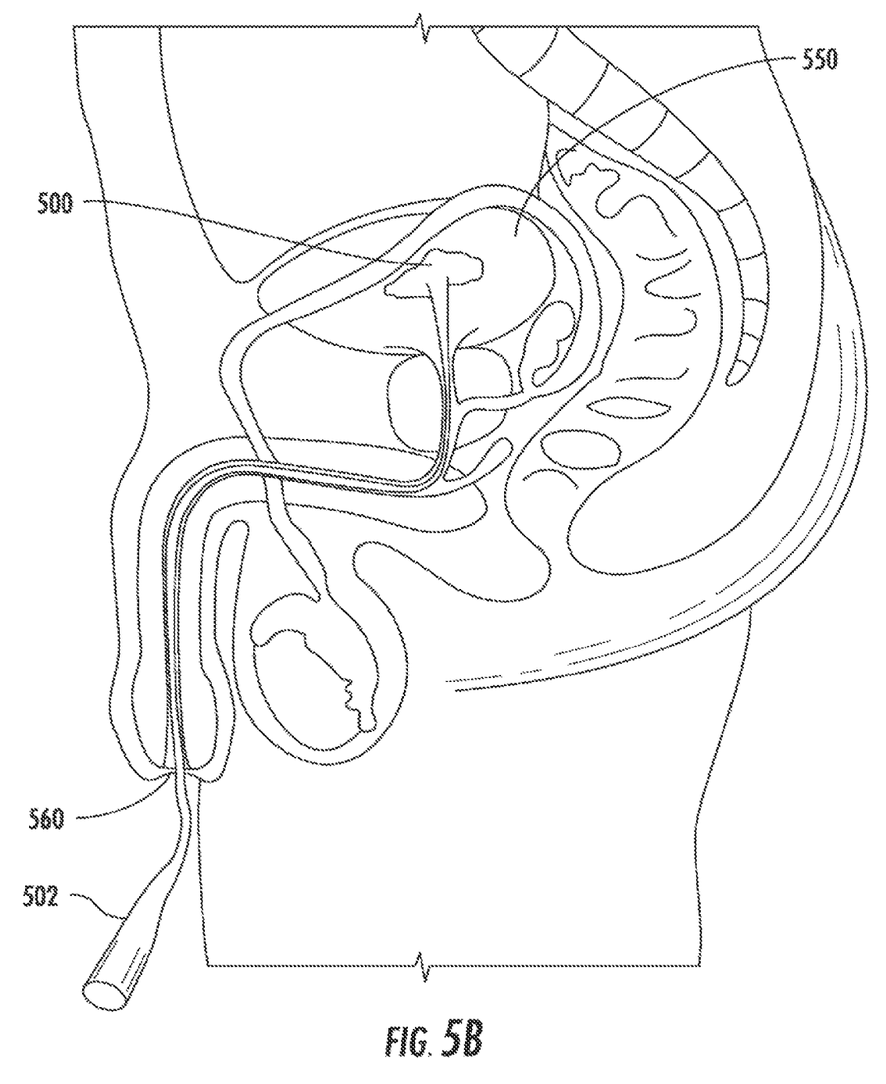
FIG. 5B illustrates a method of applying a coating material onto to the inner surface of the bladder wall for local administration of gemcitabine as described herein.
Figure 6:
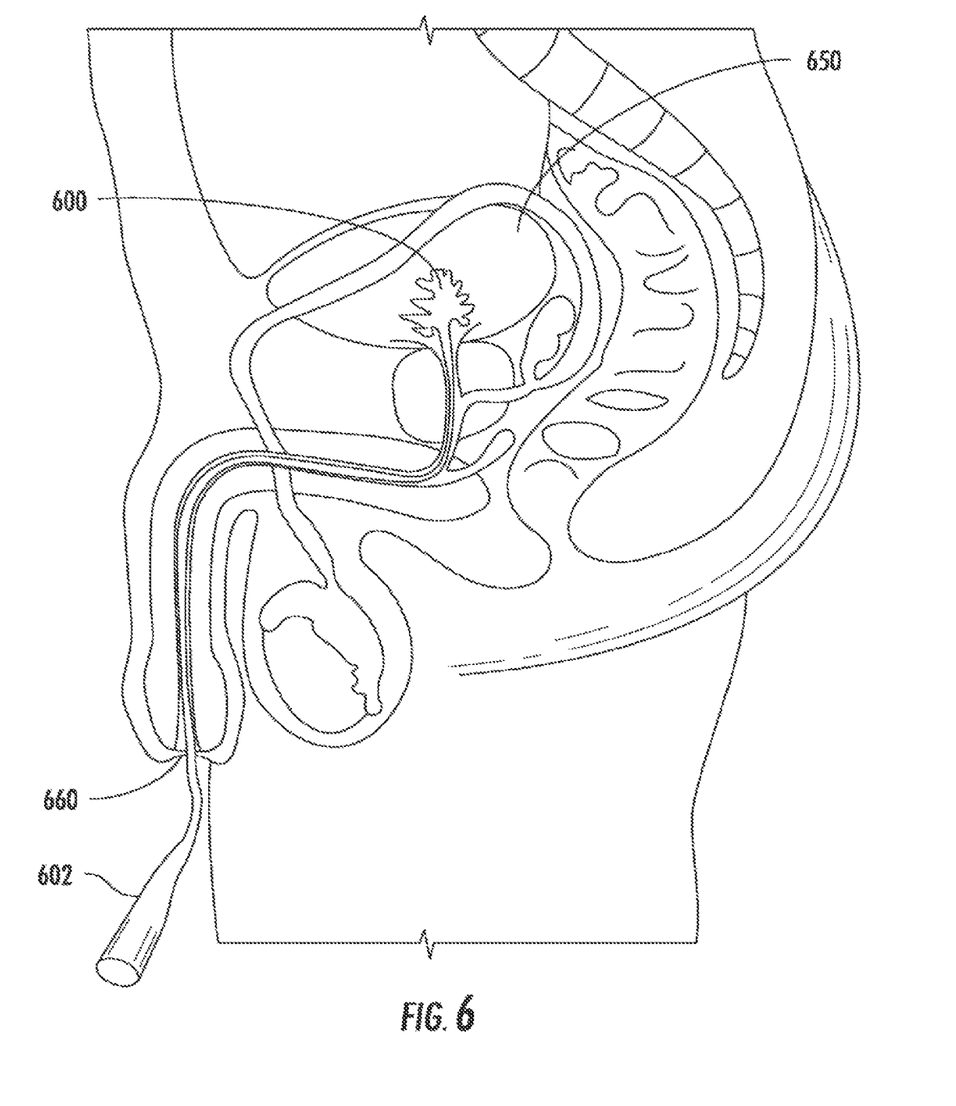
FIG. 6 illustrates a method of applying a liquid drug or drug formulation into the bladder.

The coating substance may be deployed in the bladder using a deployment instrument. FIG. 5B is a sagittal view of a male genitourinary system, illustrating a coating substance 500 being deployed through a deployment instrument 502 into an implantation site. By way of example, the male anatomy is shown and the implantation site is shown as the bladder 550. The coating substance 500 may be an embodiment of one of the coating substances described herein. The deployment instrument 502 may be any device designed to navigate natural lumens of the body to reach the intended implantation site. For deployment in the bladder 550, the deployment instrument 502 is sized and shaped for passing through a urethra 560 of a patient to a bladder 550 as shown. The deployment instrument 502 may be a known device, such as a catheter or cystoscope, or a specially designed device. The deployment instrument 502 is used to deploy the coating substance 500 into the body and is subsequently removed from the body, leaving the coating substance 500 wholly implanted in the body. Once so implanted, the coating substance 500 may release drug into the body for an extended period. A comparable procedure can be used to deploy any of the devices or drugs described herein into other parts of the body through other natural lumens. For example, as shown in FIG. 6, a deployment instrument 602 can be used to deploy a liquid drug or drug formulation 600 into the bladder 650 by passing the deployment instrument 602 through a urethra 660.

In one embodiment, a second therapeutic agent is administered to the patient. The second therapeutic agent may be administered intravesically. The methods and systems described herein may be used to administer the second therapeutic agent intravesically. The second therapeutic agent may include a cytotoxic agent, an analgesic agent, an anti-inflammatory agent, or a combination thereof. In one embodiment, the second therapeutic agent prevents, treats, or ameliorates cystitis of the bladder.

The intravesical methods and systems described herein also may be used to deliver therapeutic concentrations to bladder-regional tissues besides the prostate. For example, maintaining a drug urine concentration at a certain level may achieve therapeutic concentrations of drug in the ureters, kidneys, urethra, lower portions of the peritoneum, regional lymph nodes, uterus, ovaries, distal portions of large bowel, including the rectum and pelvic floor musculature.

The term "patient" as used herein refers to humans or other mammals, such as in veterinary or livestock applications. In a particular embodiment, the patient is an adult human male.

The present invention may be further understood with reference to the following non-limiting examples.

Example 1

Gemcitabine Prostate Uptake from Bladder

A study was conducted on male Sprague Dawley rats administering $^{14}$C gemcitabine by intra-urinary bladder cannula, over a 6- or 24-hour continuous perfusion, or by a single IV bolus. The 6- and 24-hour continuous perfusions perfused 6.9 and 26.6 mg, respectively, of gemcitabine into the bladder. The single IV bolus included 5.0 mg of gemcitabine.

Figure 7:
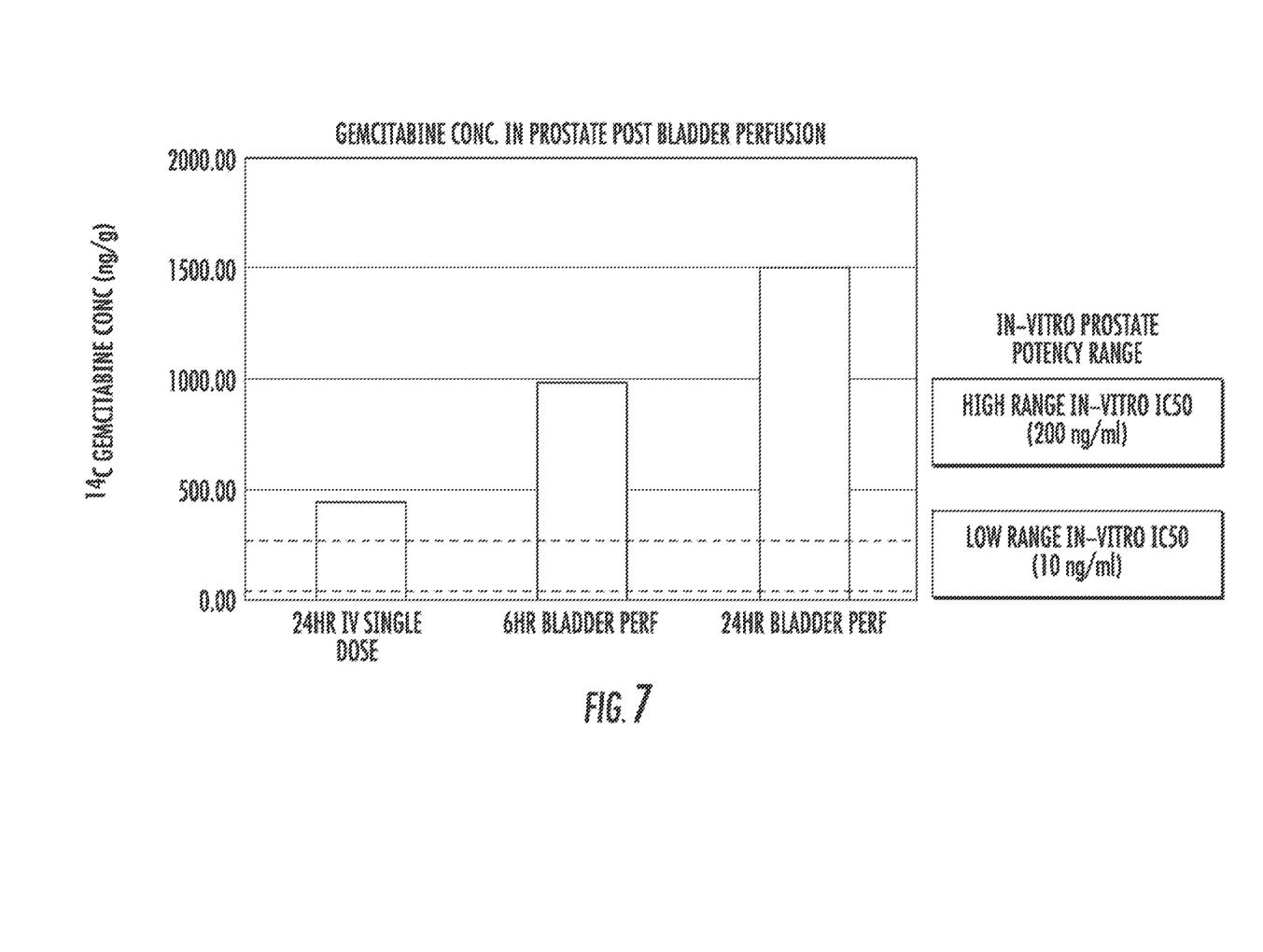
FIG. 7 illustrates the concentration of gemcitabine in the prostate after bladder perfusion and intravenous administration.
Figure 8:
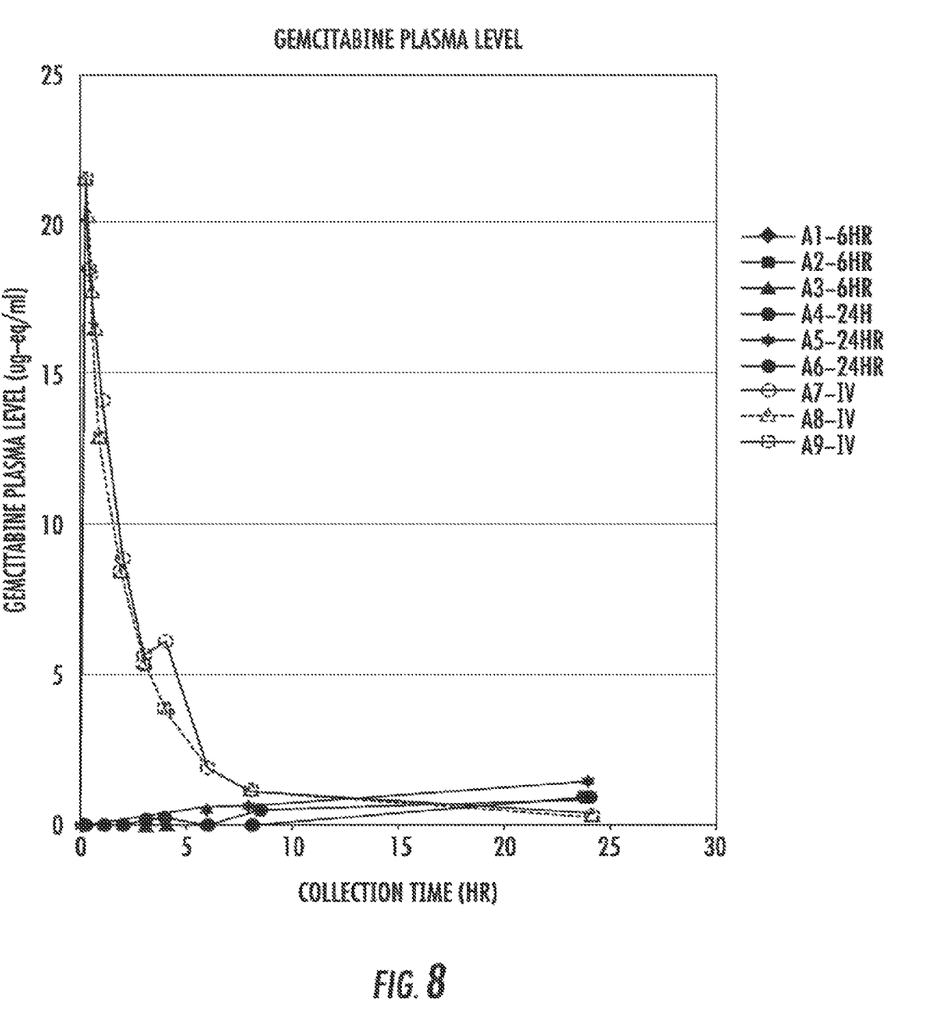
FIG. 8 illustrates the plasma levels of gemcitabine after bladder perfusion and intravenous administration.
Figure 9:
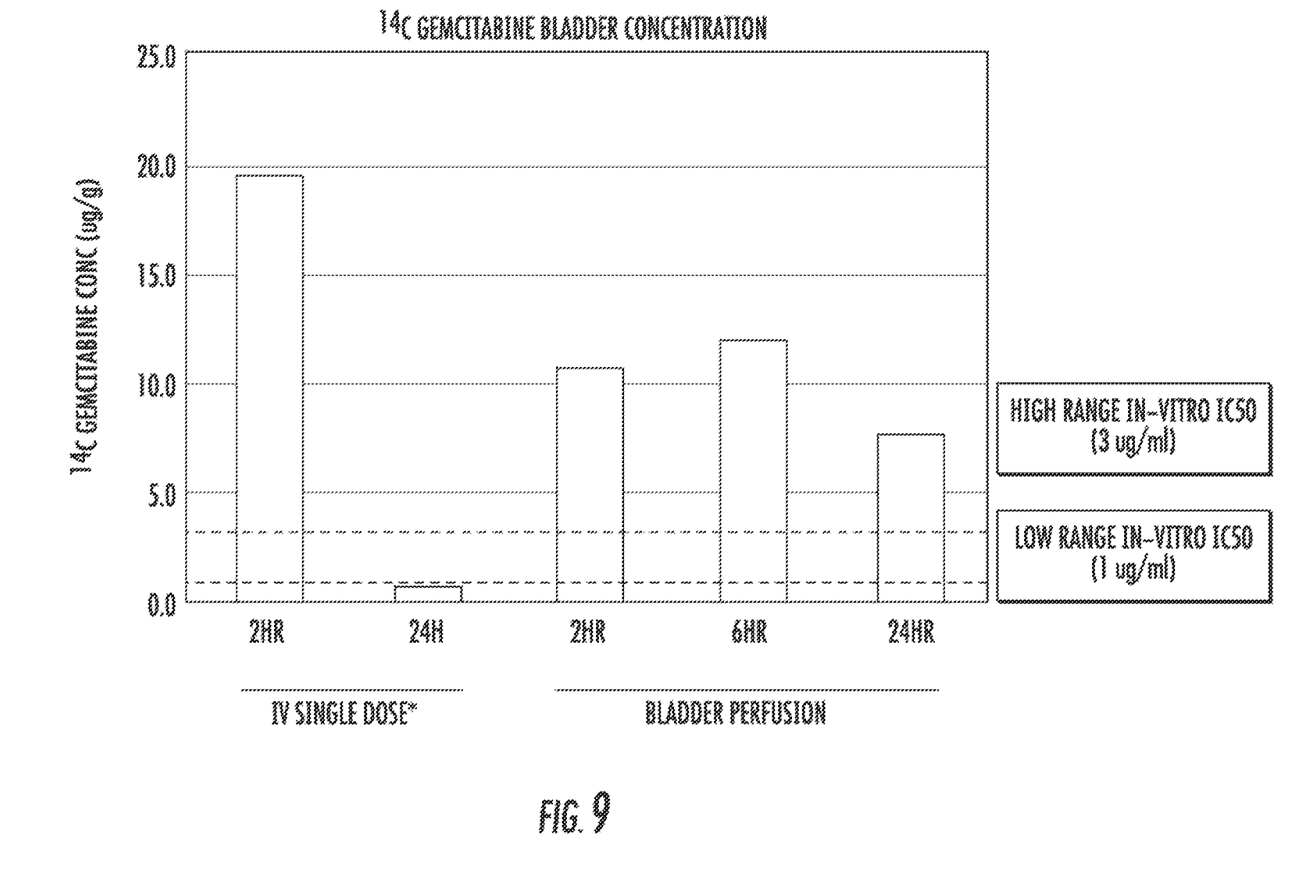
FIG. 9 illustrates $^{14}C$ gemcitabine concentration in the bladder after bladder perfusion and intravenous administration.

Blood (FIG. 8), urine, and tissue samples (e.g., bladder, prostate)(FIGS. 7 and 9) were collected and analyzed for gemcitabine content. The results are illustrated in FIGS. 7-9. The results show that sustained gemcitabine urine concentrations have been found to produce significant gemcitabine levels in bladder tissue, which are at or exceed therapeutic concentrations based on in vitro bladder cancer cell experiments. The gemcitabine levels in the bladder are shown in FIG. 9, which also depicts a significantly lower concentration of gemcitabine in the bladder 24 hours after a clinically relevant IV dose.

Similar and unexpected results have been observed in prostate tissue, as shown in FIG. 7. In particular, prostate gemcitabine tissue concentrations are substantially higher than those observed after IV administration. Furthermore, the absolute tissue levels are well above the concentrations shown to kill prostate cancer cells in vitro, which range from 10 ng/mL to 200 ng/mL.

In contrast, it is noted that Phase 2 clinical studies of gemcitabine prostate cancer patients have shown limited efficacy. It is also noted that animal studies have shown liposomal formulations of gemcitabine dramatically enhance efficacy—which activity was thought to be the result of improved tumor exposure, because (i) liposomes may protect gemcitabine from rapid metabolism, and (ii) liposomes may improve gemcitabine prostate tissue concentrations. Accordingly, in view of the present animal study, which shows the unexpected accumulation of gemcitabine in prostate tissue following administration of gemcitabine in urine, it is believed that intravesical delivery of gemcitabine will produce superior gemcitabine efficacy in prostate cancer without significant systemic exposure.

Example 2

Limited Prostate Uptake of Cisplatin and Oxaliplatin from Bladder

Figure 10:
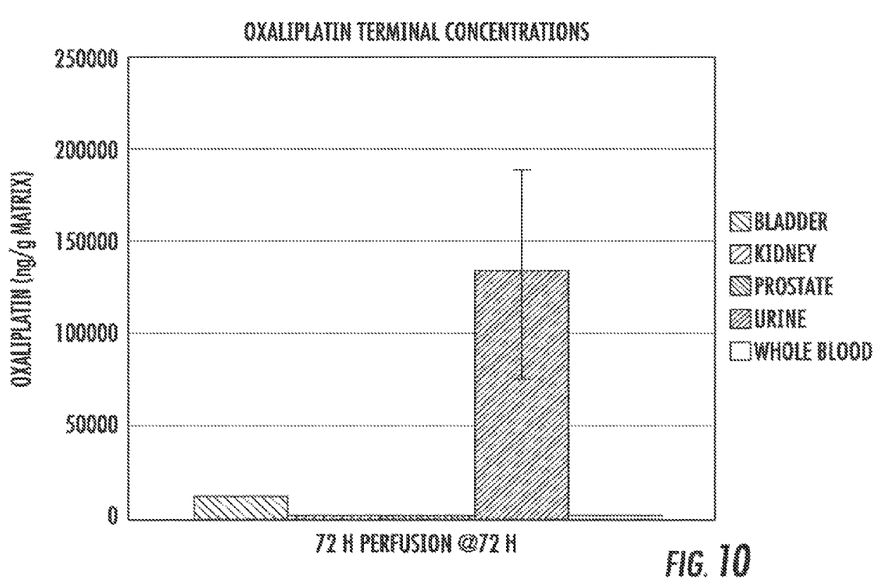
FIG. 10 illustrates oxaliplatin terminal concentrations after bladder perfusion.
Figure 11:
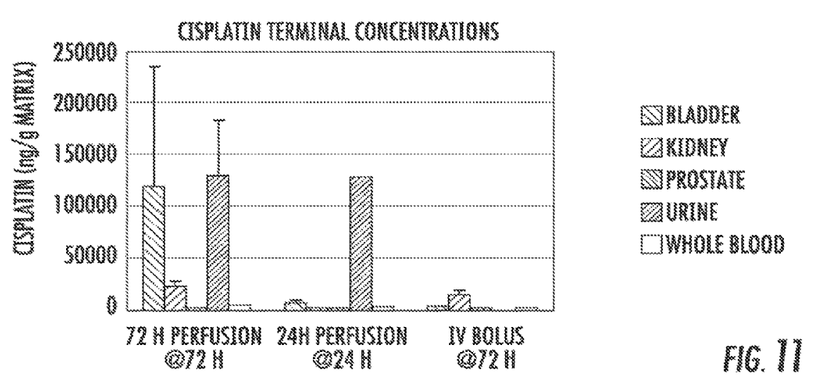
FIG. 11 illustrates cisplatin terminal concentrations after bladder perfusion and intravenous administration.

In a similar study to Example 1 oxaliplatin or cisplatin were administered to male Sprague Dawley rats by intra-urinary bladder cannula, over a 6- or 24-hour continuous perfusion, or by a single IV bolus. As shown in FIG. 10 and FIG. 11, oxaliplatin and cisplatin prostate partitioning, although achieving therapeutic bladder concentrations and kidney concentrations following cisplatin, exhibit poor partitioning into the prostate.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

I claim:

1. A method of treatment of the prostate comprising:
   locally administering gemcitabine into the urinary bladder of a patient having a prostate in need of treatment to achieve a sustained concentration of the gemcitabine in urine in the bladder sufficient to produce a therapeutic concentration of the drug in the prostate,
   wherein the locally administering into the patient's bladder is at a mean average amount of from 1 mg/day to about 300 mg/day of the gemcitabine.

2. The method of claim 1, wherein the locally administering into the patient's bladder is continuous.

3. The method of claim 2, wherein the locally administering into the patient's bladder is continuous over a period of at least 2 hours.

4. The method of claim 1, wherein the locally administering into the patient's bladder is intermittent.

5. The method of claim 1, wherein the patient is in need of treatment for prostate cancer.

6. The method of claim 1, wherein the gemcitabine is delivered into the bladder from an intravesical drug delivery device which continuously releases the gemcitabine into the urine in the bladder over a sustained period.

7. The method of claim 6, wherein the sustained period is at least 2 hours.

8. The method of claim 6, wherein the sustained period is from 1 day to 14 days.

9. The method of claim 6, wherein the intravesical drug delivery device comprises a housing which contains and controllably releases the gemcitabine and which is elastically deformable between a retention shape configured to retain the device in the patient's bladder and a deployment shape for passage of the device through the patient's urethra.

10. The method of claim 9, wherein the gemcitabine contained in the housing is in a non-liquid form.

11. The method of claim 10, wherein the non-liquid form is selected from the group consisting of tablets, granules, semisolids, capsules, and combinations thereof.

12. The method of claim 1, wherein the drug is delivered into the bladder from a coating substance applied to the bladder, which coating substance releases the gemcitabine into the urine in the bladder over a sustained period.

13. The method of claim 12, wherein the coating substance comprises a mucoadhesive formulation.

14. The method of claim 1, wherein the locally administering comprises pumping a liquid form of the gemcitabine into the bladder through a urethral catheter which is deployed into the bladder.

15. The method of claim 1, wherein the locally administering into the patient's bladder is from 1 mg/day to 100 mg/day of the gemcitabine for up to 7 days.

16. The method of claim 1, wherein the locally administering into the patient's bladder is from 20 mg/day to 300 mg/day of the gemcitabine for up to 7 days.

17. A method of administering gemcitabine to a patient in need of treatment of prostate cancer, the method comprising:
   locally administering gemcitabine into the bladder of a patient to achieve a sustained concentration of the gemcitabine in urine in the bladder sufficient to produce a therapeutic concentration of the gemcitabine in the prostate,
   wherein the gemcitabine is administered into the bladder from an intravesical drug delivery device which continuously releases the gemcitabine into the urine in the bladder over a sustained period.

18. The method of claim 17, wherein the intravesical drug delivery device releases from 20 mg/day to 300 mg/day of the gemcitabine for up to 7 days.

19. The method of claim 17, further comprising administering at least a second therapeutic agent to the patient.

20. The method of claim 19, wherein the second therapeutic agent is administered intravesically.

21. The method of claim 19, wherein the second therapeutic agent comprises a cytotoxic agent, an analgesic agent, an anti-inflammatory agent, or a combination thereof.

* * * * *